| (12) | United States Patent | (10) Patent No.: | US 9,032,954 B2 |
|---|---|---|---|
| | Bernstein | (45) Date of Patent: | May 19, 2015 |

(54) ANESTHESIA MACHINE $CO_2$ ABSORBER BYPASS

(71) Applicant: Jerome Bernstein, Boynton Beach, FL (US)

(72) Inventor: Jerome Bernstein, Boynton Beach, FL (US)

( * ) Notice: Subject to any disclaimer, the term of this patent is extended or adjusted under 35 U.S.C. 154(b) by 145 days.

(21) Appl. No.: 13/629,995

(22) Filed: Sep. 28, 2012

(65) Prior Publication Data

US 2014/0034050 A1 Feb. 6, 2014

Related U.S. Application Data

(60) Provisional application No. 61/626,652, filed on Oct. 1, 2011.

(51) Int. Cl.
```
A62B 7/10      (2006.01)
A62B 23/02     (2006.01)
A61M 16/01     (2006.01)
A61M 16/10     (2006.01)
A61M 16/20     (2006.01)
A61M 16/22     (2006.01)
A61M 16/00     (2006.01)
A61M 16/08     (2006.01)
```

(52) U.S. Cl.
CPC ............. A61M 16/01 (2013.01); *A61M 16/208* (2013.01); *A61M 16/22* (2013.01); A61M 16/1075 (2013.01); *A61M 16/0078* (2013.01); *A61M 16/20* (2013.01); *A61M 16/0891* (2014.02)

(58) Field of Classification Search
CPC ..................................................... A61M 16/22
USPC ........................................ 128/205.28, 205.27
See application file for complete search history.

(56) References Cited

U.S. PATENT DOCUMENTS

| 3,556,097 | A | * | 1/1971 | Wallace .................... | 128/202.23 |
|---|---|---|---|---|---|
| 4,791,922 | A | * | 12/1988 | Lindsay-Scott et al. . | 128/205.28 |
| 5,706,799 | A | * | 1/1998 | Imai et al. ................ | 128/205.12 |
| 6,095,135 | A | * | 8/2000 | Clawson et al. .......... | 128/201.13 |
| 6,131,571 | A | * | 10/2000 | Lampotang et al. ..... | 128/204.21 |
| 7,007,693 | B2 | * | 3/2006 | Fuhrman et al. ......... | 128/205.12 |
| 7,077,136 | B2 | * | 7/2006 | Ahlmen et al. .......... | 128/205.27 |
| 7,275,541 | B2 | * | 10/2007 | Fukunaga et al. ....... | 128/204.18 |
| 7,424,889 | B2 | * | 9/2008 | Mashak .................... | 128/205.28 |
| 8,127,762 | B2 | * | 3/2012 | Loncar et al. ............ | 128/203.12 |

* cited by examiner

*Primary Examiner* — Justine Yu
*Assistant Examiner* — Kathrynn Reilly
(74) *Attorney, Agent, or Firm* — Fleit Gibbons Gutman Bongini & Bianco PL; Paul D. Bianco; Gary S. Winer (57) ABSTRACT

A $CO_2$ absorber bypass for an anesthesia machine includes a diverter for diverting exhaled gas to bypass the $CO_2$ absorber of the anesthesia machine when the diverter is activated. The $CO_2$ absorber bypass further includes a shunt for conveying the diverted exhaled gas, a coupler for connecting the shunt to the inhalation limb of the anesthesia machine, a shunt one way valve, a shunt adjustable pressure limiting valve, and a shunt reservoir. The $CO_2$ absorber bypass allows the $CO_2$ absorber to be changed while the exhalation limb conveys exhaled gas from a patient and the inhalation limb conveys gas to the patient.

20 Claims, 11 Drawing Sheets

ANESTHESIA MACHINE CO$_2$ ABSORBER BYPASS

FIELD OF THE INVENTION

The invention related to a CO$_2$ absorber bypass for an anesthesia machine and to an anesthesia machine having such a CO$_2$ absorber bypass.

BACKGROUND OF THE INVENTION

Events occurring during general anesthesia may require CO$_2$ absorber bypass. Included in these events would be situations in which the absorber granule indicator change has alerted the anesthesiologist to the need for canister replacement. In an extremely urgent situation such as malignant hyperthermia (MH) it is imperative to bypass the absorber canisters in the shortest time possible. The device according to an aspect of the present invention can be utilized whenever CO$_2$ absorber bypass is indicated and desirable.

Normally during anesthesia exhaled gases are conducted to the CO$_2$ absorber while fresh gases are conducted to the patient during inhalation. Exhaled gases having been absorbed by the canisters exit the absorber and are joined with incoming fresh gases and return to the patient thereby starting a new cycle.

In present day anesthesia machines, the patient circuit prevails and exists commercially in several versions. Generally, the two limb circuit version comprises separate inhalation and exhalation limbs. A second version conducts the inhaled gases toward the patient via a manifold tube and enters a coaxial circuit in which fresh gases are conducted through an inner concentric tube while the exhaled gases are conducted through an outer concentric tube. There are other versions of anesthesia delivery utilizing absorbers and wherever bypassing the absorber is indicated the invention will suffice.

Perusal of the internet for patents in the same field of endeavor reveals the following:

A) W. C. Hamilton Mar. 2, 1954 Filed, Jun. 7, 1952 U.S. Pat. No. 2,693,181. This intra-canister container bypass requires complete overhaul or substitution of an apparently intricate, costly device, which has not been exhibited at anesthesia national conferences.

B) Chen et al United States Patent Application Publication Pub. No.: US 2009/0056720 A1 Pub. Date: Mar. 5, 2009. "Apparatus for Installing or Uninstalling Carbon Dioxide Absorbent Canister . . . comprises a body, a lifting member, and a lifting mechanism". This intra-canister container mechanism reveals an obviously radical, costly departure from standard commercially available devices, wherein currently the CO$_2$ absorbent canisters are disposables, this device requires a complete overhaul of prevailing practice. Like "A", this patent has not been marketed to practitioners of anesthesia.

Neither of these patents have claims for pre- or post-canister container sites. Both prior art bypass attempts require both hands to be utilized during the maneuvers. The bypass according to an embodiment of the present invention can be accomplished using one hand or, when utilized automatically, neither hand.

SUMMARY OF THE INVENTION

It is an aspect of the invention to bypass the CO$_2$ absorber. In the double limb version, a diverter means will shunt a breath across the patient circuit containing a unidirectional valve, APL (pop-off valve), and "T" connector. The coaxial version will have a directional valve, APL valve, diverter with shunt and "T" connector. Whenever parts of the original patient circuit are bypassed they will be replaced in the bypass circle. While it appears redundant, they are inserted into the circuit in order to maintain functionality. The parts can be inserted into the circuit as separate attachments, in fixed or disposable options The bypass can be situated distal to the exhalation/unidirectional and inhalation/unidirectional valve. Various locations for its components can be selected along the circuit path.

DETAILED DESCRIPTION OF THE INVENTION

The device bypasses the CO$_2$ absorber of the patient circuit. It utilizes the original directional valve and APL valve when situated distal to the patient. It utilizes a diverter means, a shunt means and a connector means conducting a breath to the inhalation limb of the patient circuit. In the proximal situation, the embodiments consist of a diverter means, a shunt means, a directional valve, and a connector means. Components which become excluded by the bypass can be included in the device bypass according to the invention in order to reestablish function of the bypassed components. The embodiments of proximal sites can be disposable aiming to minimize cross-contamination and to maximize good hygienic outcomes. Cooling means and automatic actuation can be included.

In distal embodiments there are:
1) Post-canister container sites, in which an embodiment of the invention begins and begins or ends after the unidirectional valve and APL valve and begins or ends after the canister and before the fresh gas inlet.
2) Pre-canister container sites, in which an embodiment of the invention begins or ends after the unidirectional valve and APL valve and begins or ends after the fresh gas inlet.
3) At the fresh gas inlet, in which an embodiment of the invention begins or ends at the fresh gas inlet and begins or ends at the inhalation route.

Figure 1:
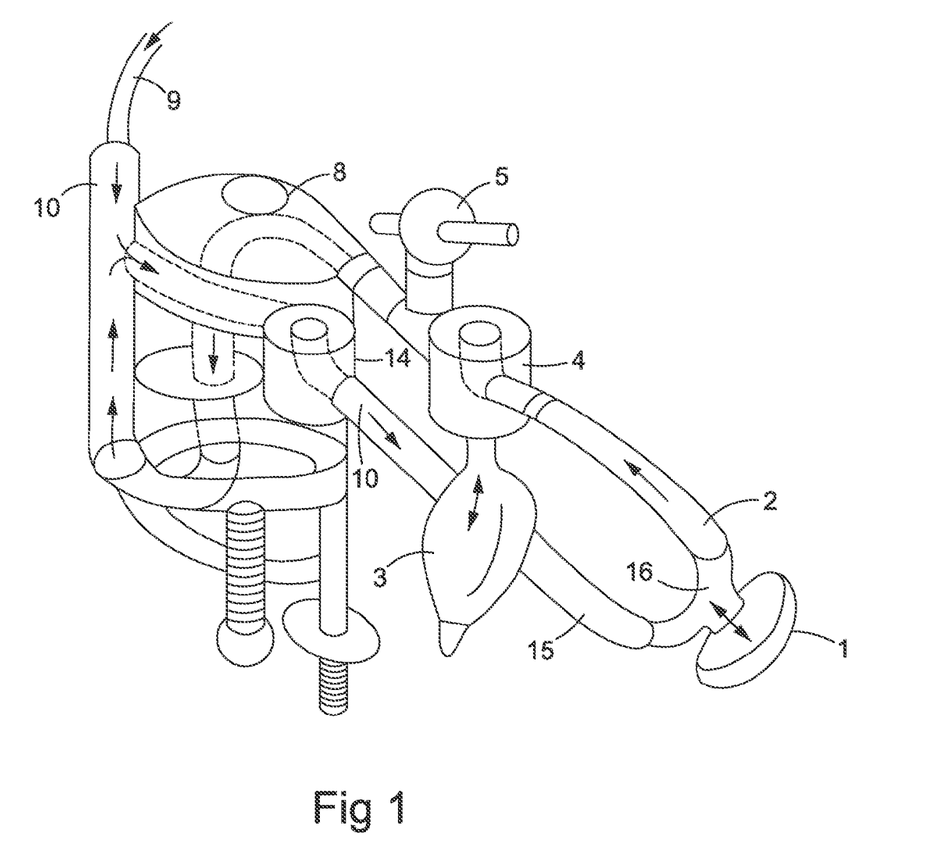
FIG. 1 is a diagram of a typical double limbed patient circuit.

In current common usage as shown in FIG. 1, an exhaled breath from the patient travels from the patient (mask tracheal tube, LMA, etc.) 1, through the exhalation limb 2, through the reservoir (bag or ventilator connector) 3, through the exhalation/unidirectional valve 4, where it progresses onward through the APL valve 5, $CO_2$ canister 8, joins the incoming gases at connection 9, passes through inhalation/unidirectional valve 14, through the patient inhalation limb 15, and return to the patient via "Y" piece 16, and the cycle is repeated.

Figure 2:
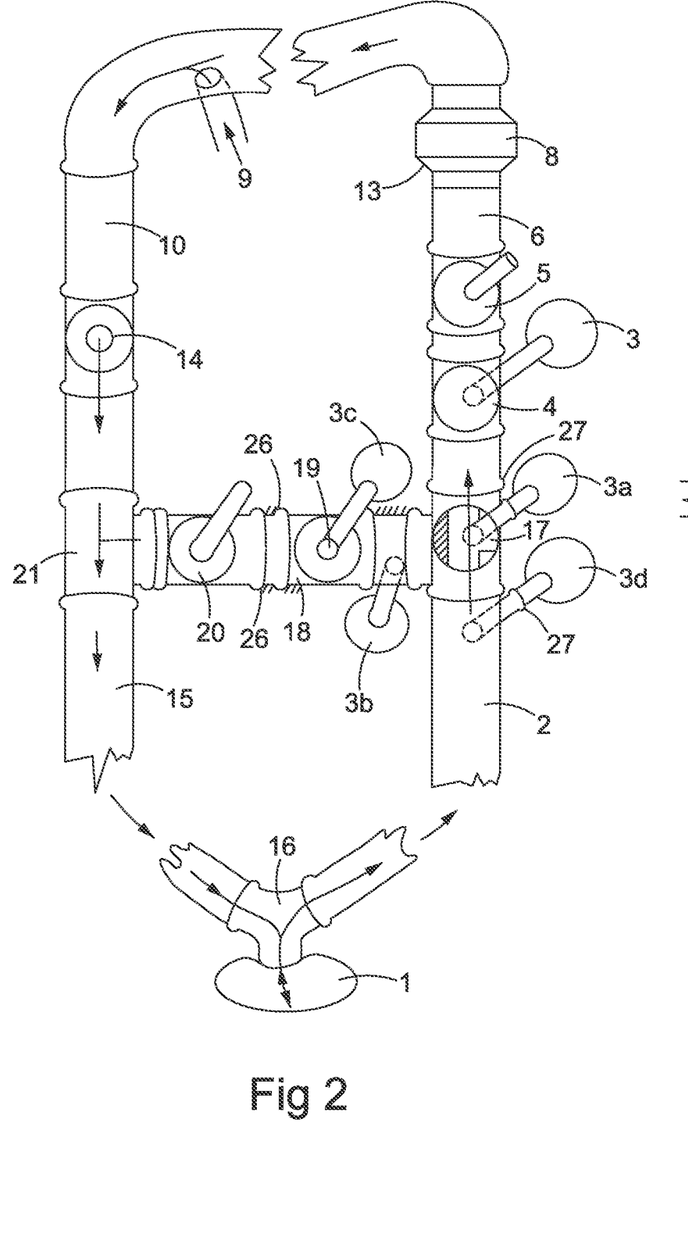
FIG. 2 is a diagram of a double limbed patient circuit having a CO$_2$ absorber bypass according to the present invention.

FIG. 2, a double limbed circuit, shows an exhaled breath from a patient 1, flows through the exhalation tube 2, through the embodiment of diverter means 17, through the unidirectional valve 4, reservoir bag 3, APL valve 5, onward through the $CO_2$ absorber 8, continues past and joining with the incoming fresh gases from inlet 9, through the anesthesia machine inhalation limb 10, through the inhalation/unidirectional valve 14, through the bypass "T" connector 21, through the inhalation tube 15, onward to the patient and thus repeating the cycle.

Figure 2A:
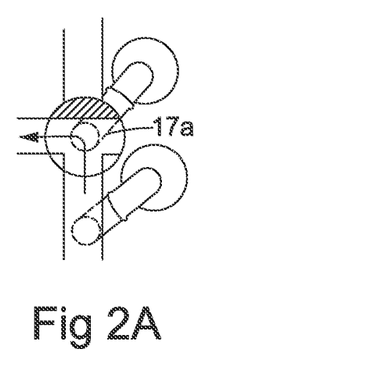
FIG. 2A is an enlarged diagram showing the bypass path of FIG. 2.

In bypass mode, the path is directed by the diverter means 17 through alternate direction mode inset 17a (see FIG. 2A), through the bypass shunt 18, shunt unidirectional valve 19, and shunt APL valve 20, and admixes at connector 21 with confluent gases coming from fresh gas inlet 9, and onward through inhalation tube 15, back to the patient's mask via "Y" tube 16, thus repeating the cycle. A reservoir bag can be placed at any site selected as shown in FIG. 2.

The redundancy of illustrated embodiments of the unidirectional valve and APL valve and some stopped and unstopped versions of the reservoir bag in the bypass and other sites is necessary whenever restoration of lost function is indicated, considering that some components can be bypassed in alternate direction mode 17a when the bypass is actuated.

The invention is intended for any and all circumstances in which $CO_2$ canister bypass is indicated and/or desirable.

Noteworthy are some optional sites for the shunt reservoir bag 3a, 3b, 3c, and 3d and 3e. At positions 3a and 3d for example the reservoir bag is stopped 27, during normal use.

Cooling means 26, automatic operation of the diverting means, and disposable parts and combinations of the invention are optional.

Prevailing anesthesia equipment utilizes corrugated flexible disposable tubing. While this is adequate for the invention, the parts thereof may consist of any materials that serve the purpose of the invention.

Figure 3:
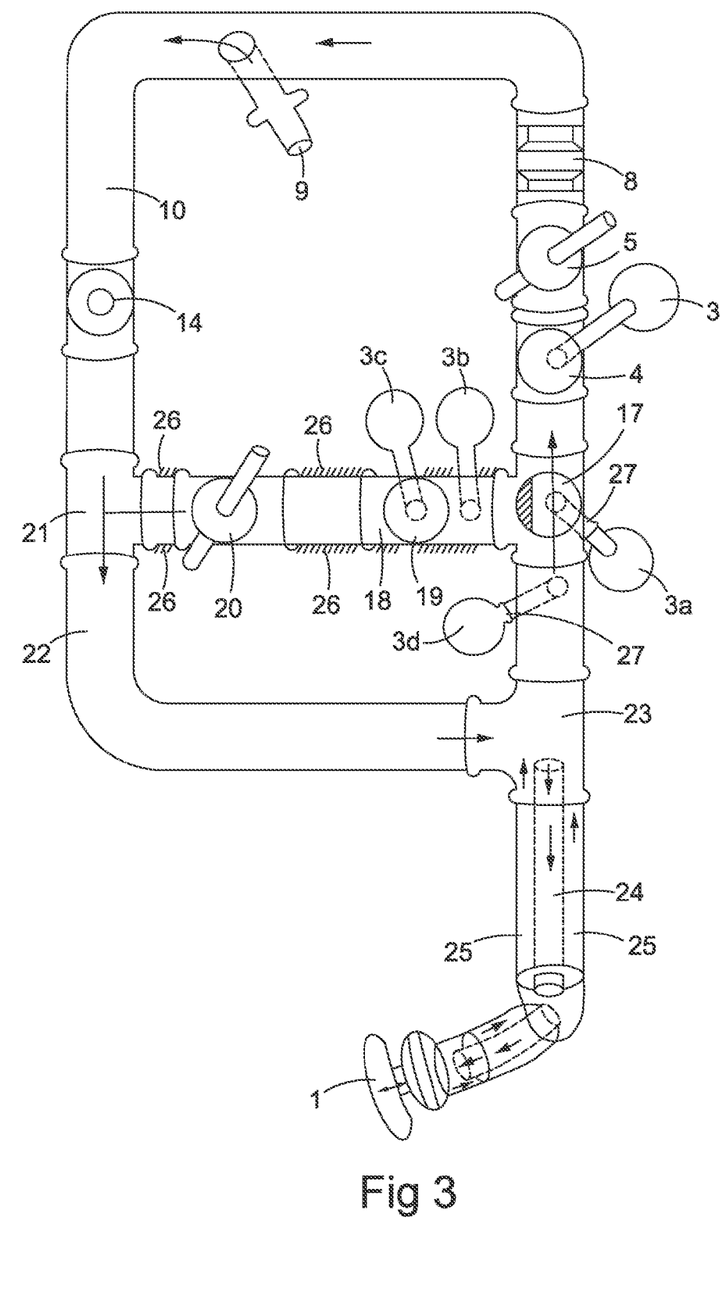
FIG. 3 is a diagram of a single limbed patient circuit having a CO$_2$ absorber bypass according to the present invention.

In, FIG. 3, a coaxial breathing circuit is shown. The original (un-bypassed) pathway for the exhaled breath leads past the reservoir bag 3, exhalation/unidirectional valve 4, APL valve 5, and the diverting means 17 in the usual position passing through absorber 8, adding fresh gas at 9, and returning to patient 1.

Figure 3A:
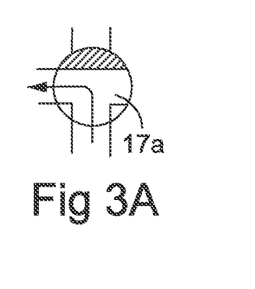
FIG. 3A is an enlarged diagram showing the bypass path of FIG. 3.

In bypass mode, an exhaled breath travels through the outer concentric tube 25, progresses past chamber 23, leads the exhaled gas through the diverter means 17a through the bypass shunt 18, past the bypass unidirectional means 19, and past the bypass APL valve 20, through the "T" connector 21, which lies downstream from the inflowing fresh gases 10 and an inhalation/unidirectional valve 14. The gas flow returns to the inhalation limb of the patient circuit via the manifold tube 22, enters the coaxial chamber 23, and continues on through the inner concentric tube 24, and project onward to the patient 1.

Noteworthy are optional positioning sites for the bypass reservoir bag at 3 a-d and at any position necessary to achieve proper function. For example, at positions 3a and 3d the bag stem is stopped 27. Optional cooling fins 26 can be applied to lengths of the conductor means 18.

The bypass can be actuated automatically or manually.

Figure 4:
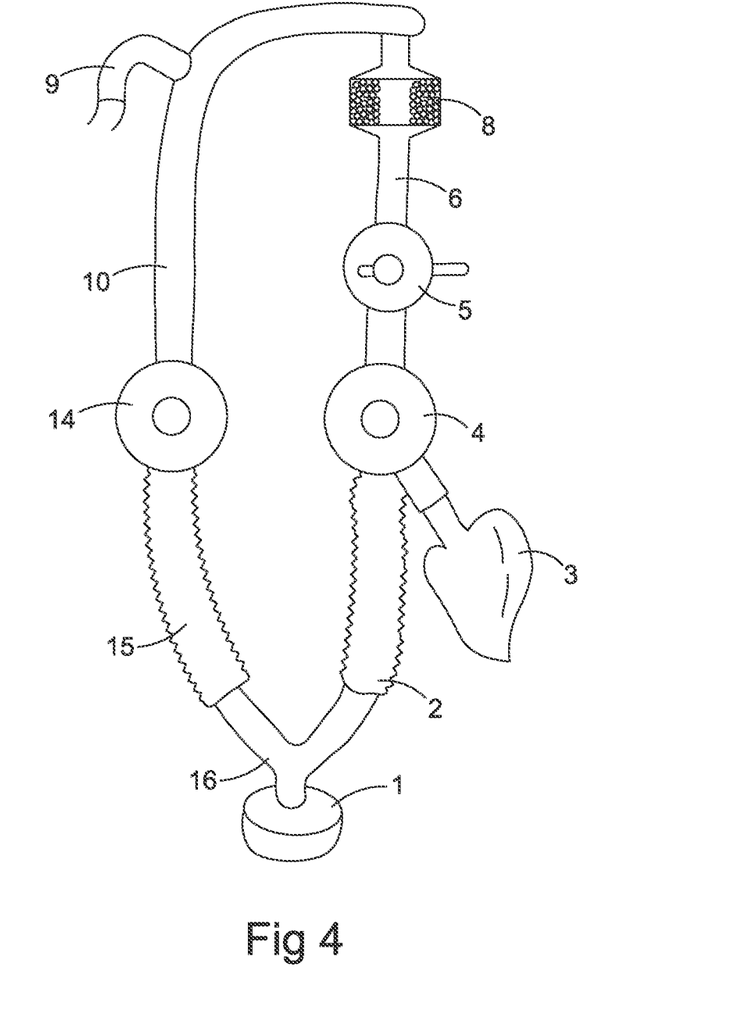
FIG. 4 is another diagram of a typical double limbed patient circuit.

In FIG. 4, the embodiment of an anesthetic patient circuit is shown in two-dimensional view. This form is utilized in subsequent illustrations.

Figure 5:
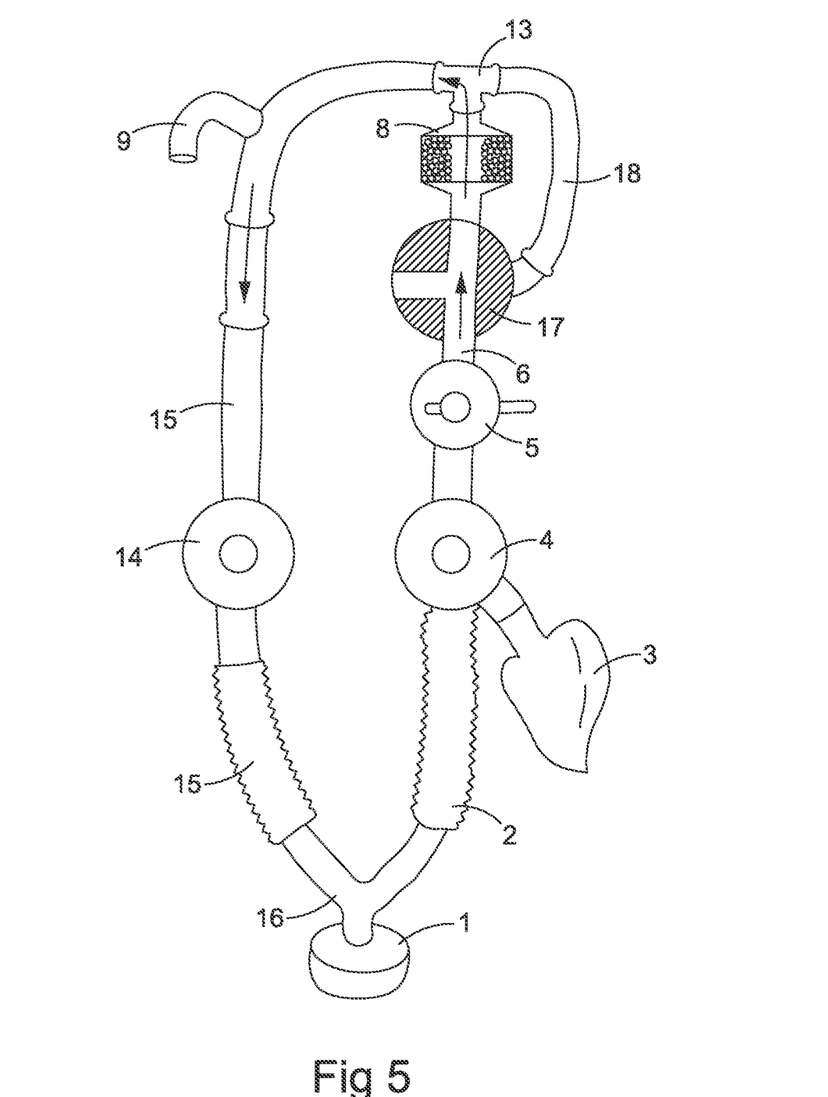
FIG. 5 is another diagram of a double limbed patient circuit having a CO$_2$ absorber bypass according to the present invention.

In FIG. 5, diverting means 17 is situated along the patient circuit pathway between the APL valve 5 of the exhalation arm of the patient circle and the $CO_2$ absorber container 8. It illustrates the usual route of gases through the diverting means 17, past the canister container through the connector means 13, and returns to the patient circle inspiration arm 15 to renew the cycle.

In FIG. 5A, diverting means 17a connects from tube 6 in bypass mode to the connector means 13, thus bypassing the canister 8.

Figure 6:
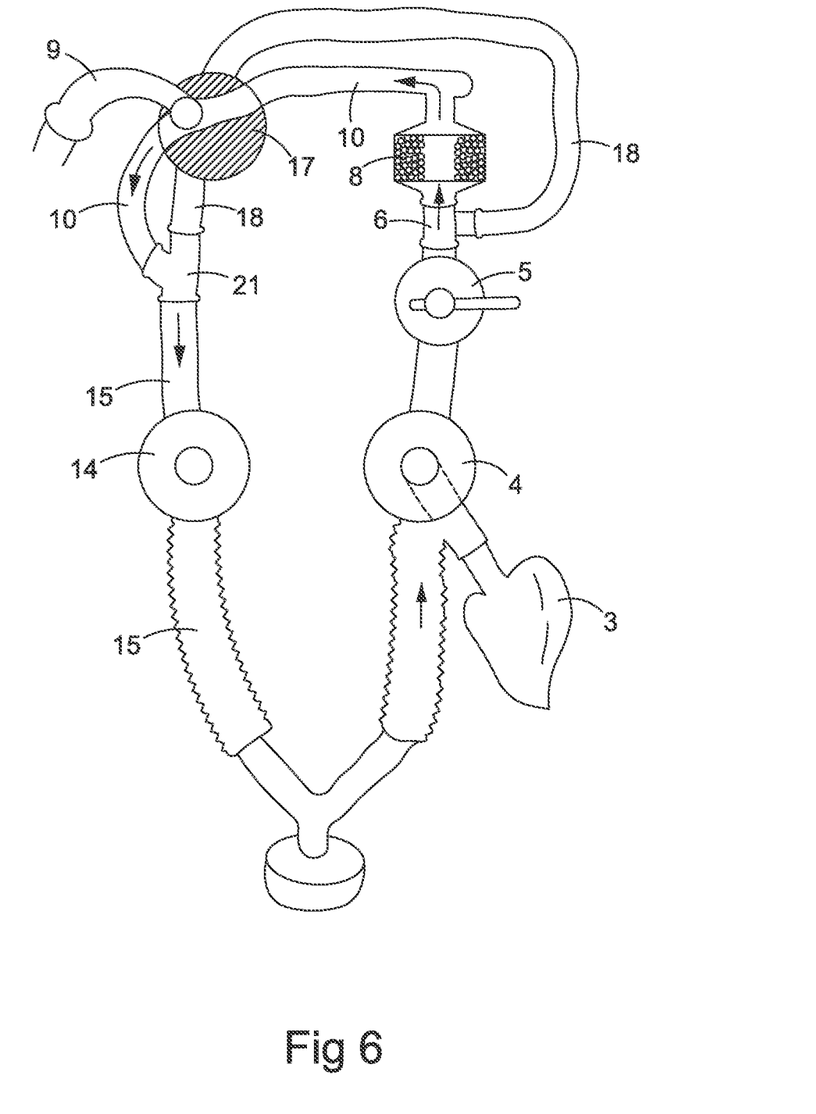
FIG. 6 is another diagram of a double limbed patient circuit having a CO$_2$ absorber bypass according to the present invention.

The usual flow path through the connector means 6, in FIG. 6 runs through canister container 8 and flows past the diverter valve means 17 through the tube 10 and on to the patient inspiration circle at connector means 21 and continues on to inhalation limb 15, and onward to the patient 1 where the circuit is completed and restarted.

Figure 7:
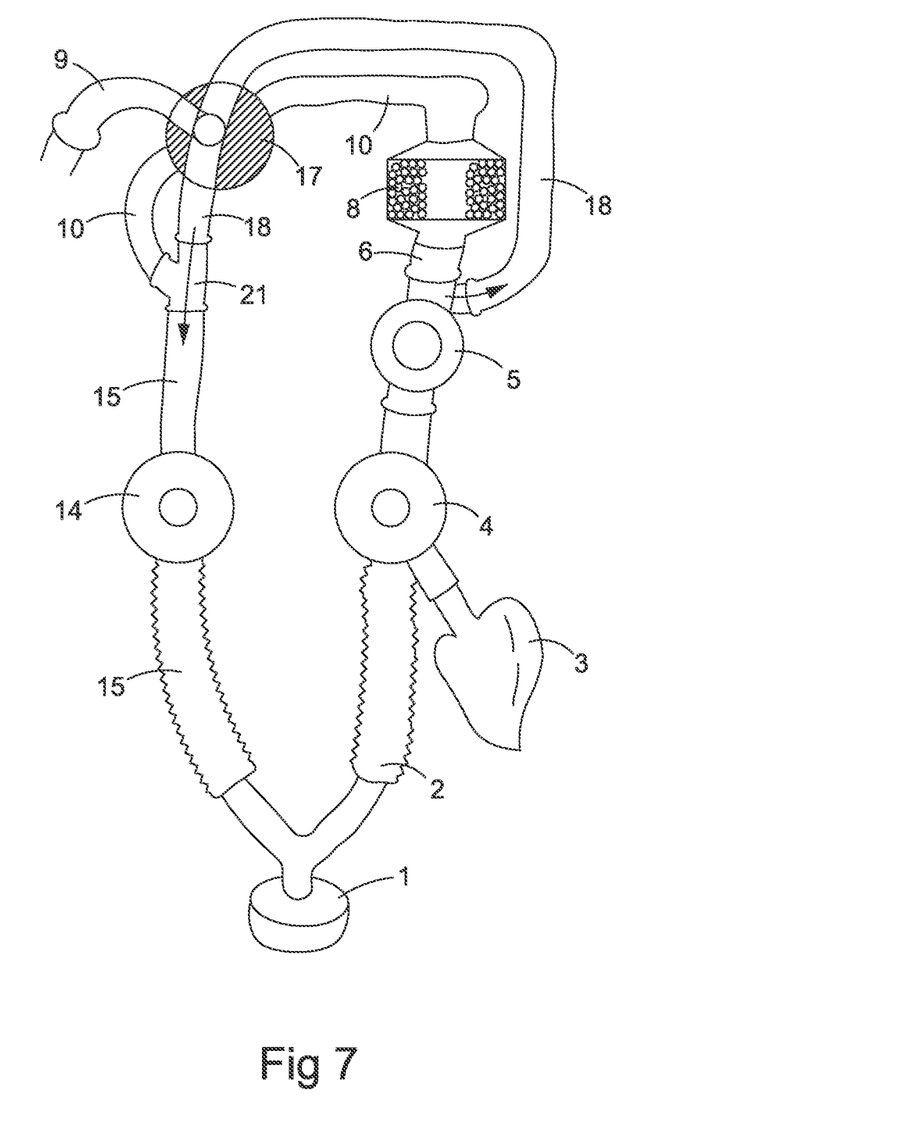
FIG. 7 is another diagram of a double limbed patient circuit having a CO$_2$ absorber bypass according to the present invention.

The flow of gases by means of connector 6 in FIG. 7 diverts the flow of gases through bypass tube 18 past the canister container 8 to the diverting means 17 which is situated at or near the fresh gas inlet port 9. Diverting means 17 is placed anywhere along the tube 10 which leads the gases exiting the absorber canister upward to join the fresh gas inlet 9 and the limb 18 which leads into the patient inhalation circle 15.

Figures 8, 8A:
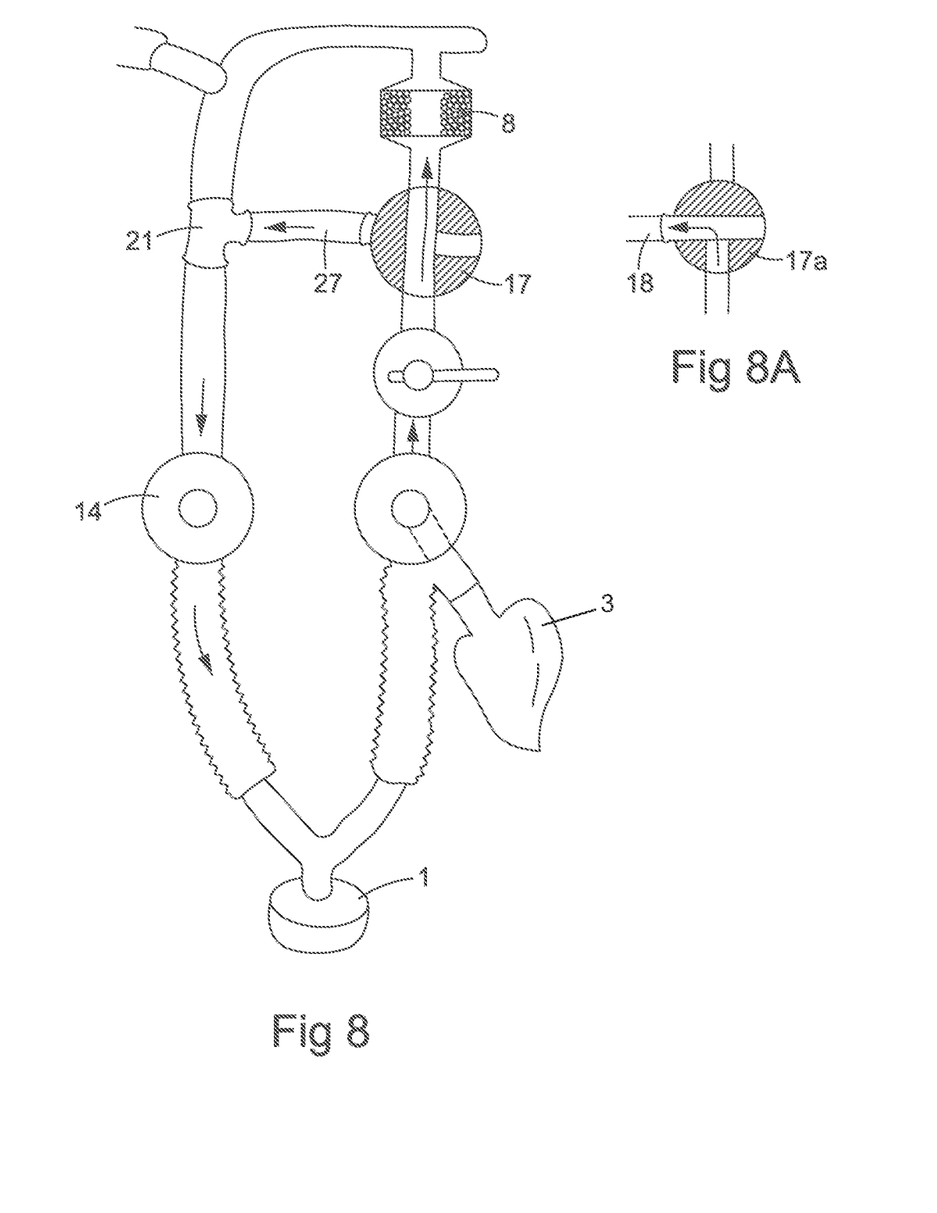
FIG. 8 is another diagram of a double limbed patient circuit having a CO$_2$ absorber bypass according to the present invention.
FIG. 8A is an enlarged diagram showing the bypass path of FIG. 8.

In FIG. 8, the usual direction of an exhaled breath is depicted showing diverter means 17 placed between the exhalation unidirectional valve and absorber 8. Bypass tube means 18 intersects with inspiration tube of the patient circle at connector means 21, and diffuses with fresh gases and is conducted through directional valve 14 and on to patient 1 reentering the patient circle.

In FIG. 8A, bypass mode is illustrated. Diverting means 17, rotated clockwise toward shunt means 18, directs a breath path at alternate route to connector "T" 21. Gases are conducted through inhalation/directional valve 14 to return to patient 1. In selected instances whenever a diverting means is utilized, automatic as well as manual controls can be opted. Symbols "T" and "Y" are interchangeable, and entail embodiments of varying angularities, flexibilities, and consistencies. They include all related connector situations.

Figure 9:
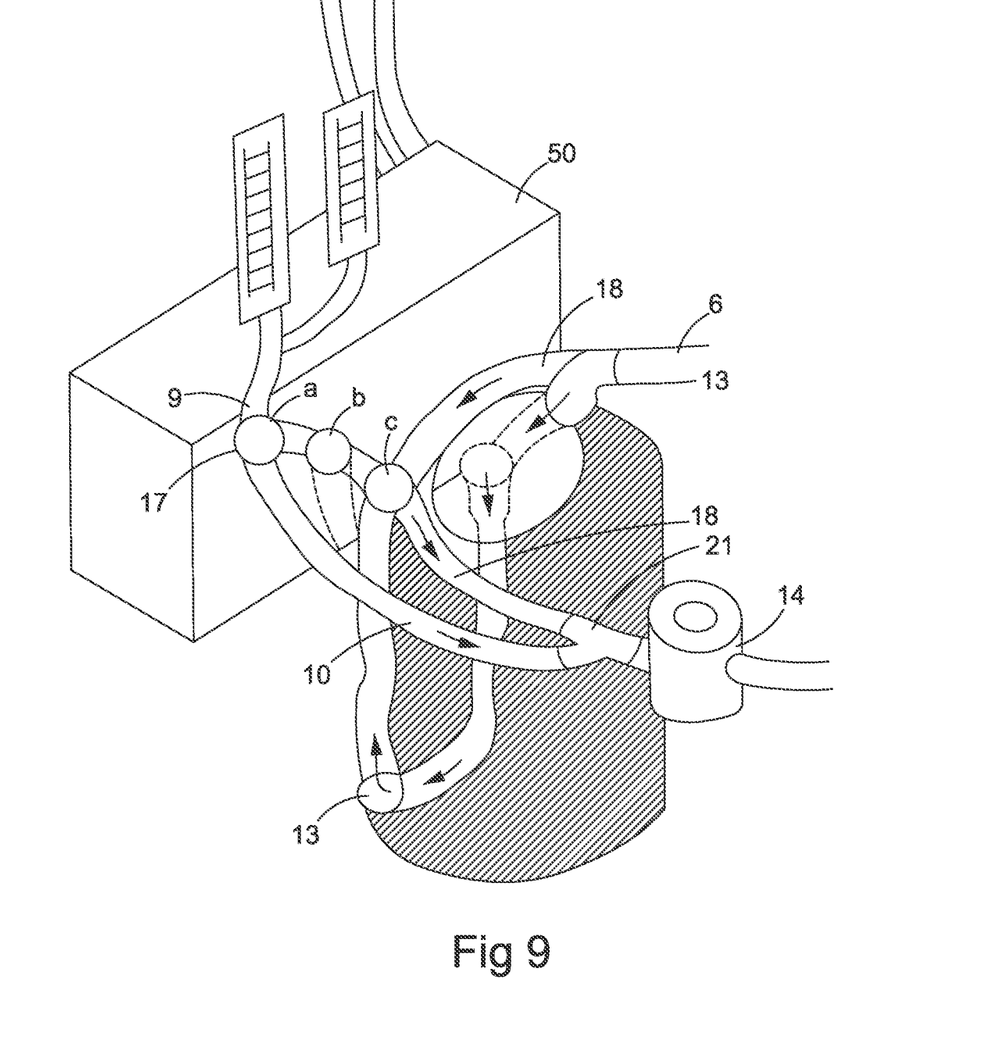
FIG. 9 is another diagram of a patient circuit having a CO$_2$ absorber bypass according to the present invention, with different possible locations for the bypass shown.

In FIG. 9, illustrated examples show infinite optional sites of diverter means 17, pre, intermediate and at canister or other nearby placements between anesthesia machine 50 and fresh gas inlet a, b, and c. Options are illustrated in un-bypassed and bypassed mode.

In un-bypassed mode gases leaving anesthesia machine 50 route through diverter means 17 pass through shunt tube 18 to intersect with "Y" connector 21, and allows flow through connector 21, travel through inhalation-unidirectional valve 14, and continue onward to patient 1 via tube 15 and the breathing cycle is repeated.

In bypassed mode gases leaving anesthesia machine 50 are directed from their original route through the fresh gas inlet to shunt tube 10 and reenter the patient inhalation limb through connector 21 and continue through directional valve 14 and continue as in the un-bypassed circuit.

Figure 10:
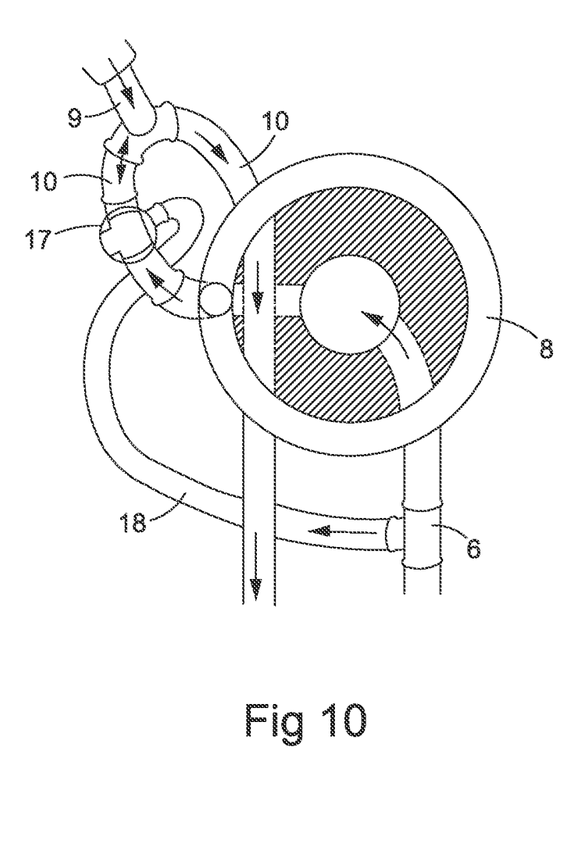
FIG. 10 is a diagram of a portion of a patient circuit having a CO$_2$ absorber bypass according to the present invention, with another location for the bypass shown.

In FIG. 10, illustrated is another option of diverter means placements between fresh gas port 9 and exhalation tube 6. The usual route of the exhaled breath passes through the absorber canister 8. It flows through the diverter means 17, diffuses with fresh gas at connector port 9, and continues its journey patient-ward through tube 10 to complete the circuit.

Figure 10A:
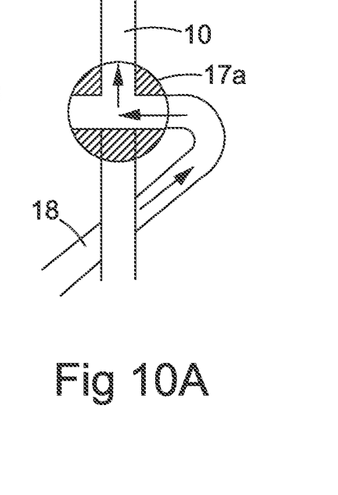
FIG. 10A is an enlarged diagram showing the bypass path of FIG. 10.
Figure 11:
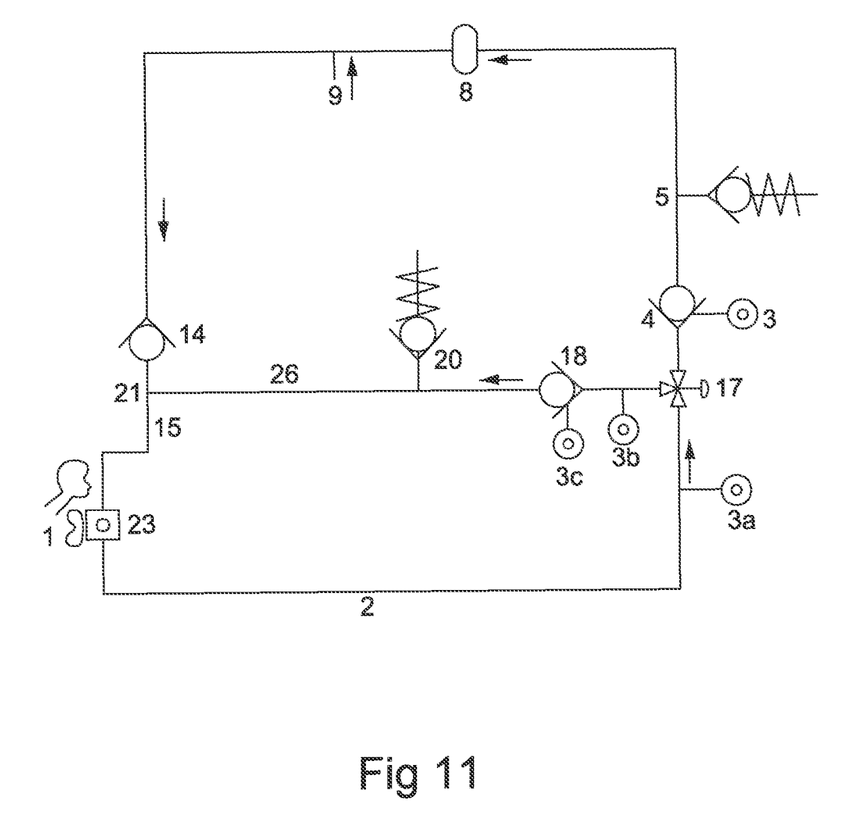
FIG. 11 is a schematic diagram of a patient circuit having a CO$_2$ absorber bypass according to the present invention.

In FIG. 10A, an exhaled breath bypasses the absorber 8 at connector 6 through tube 18, changes direction when the diverter means 17 is rotated thus detouring past the fresh gas port 9, enters tube 10 and continues its journey patient-ward through tube 10 to complete the circuit.

In summary, the device according to the present invention can be located in several locations:
1) Post-canister container site.
2) Pre-canister container site.
3) Intra-canister container site.
4) At the fresh gas inlet.
5) Proximal to the exhalation unidirectional valve and APL valve, there are varying locations of breathing reservoir. Present day usage consists of flexible disposable tubing found in either:
a) Two limb circuit.
b) Coaxial circuit.

Rapid removal of the $CO_2$ absorber from the patient circuit during general anesthesia is sometimes necessary. In order to maintain uninterrupted breathing, bypass of the patient circuit is required. This is accomplished by positioning a diverter means, shunt means, and "T" connector means. In circumstances in which the unidirectional valve, APL valve and connector and reservoir bag are omitted from the circuit, they can be restored as parts of the bypass, thus retrieving function which would have been lost had they not been included.

Various sites for the reservoir bag can be chosen. The device can be disposable to prevent cross contamination. The scope of this invention covers bypass of the $CO_2$ absorber in times of acute emergency, and on all occasions when $CO_2$ canister bypass is indicated.

Cooling fins and automatic actuation are optional embodiments.

The invention claimed is:

1. A $CO_2$ absorber bypass for an anesthesia machine having an exhalation limb for conveying exhaled gas from a patient through a reservoir, a one way exhalation valve, and an adjustable pressure limiting valve to an entry port of a $CO_2$ absorber, an exiting port of the $CO_2$ absorber coupled to a connector for incoming gas, the connector coupled to an inhalation limb through a one way inhalation valve, the inhalation limb for conveying gas to the patient, the $CO_2$ absorber bypass comprising:
a diverter for diverting exhaled gas to bypass the $CO_2$ absorber when the diverter is activated, the diverter being located upstream the one way exhalation valve;
a shunt for conveying the diverted exhaled gas;
a coupler for connecting the shunt to the inhalation limb;
a shunt one way valve located between the coupler and diverter;
a shunt adjustable pressure limiting valve; and
a shunt reservoir,
wherein the $CO_2$ absorber bypass allows the $CO_2$ absorber to be changed while the exhalation limb conveys exhaled gas from a patient and the inhalation limb conveys gas to the patient,
wherein the shunt is located between the coupler and the diverter with a first end at the coupler and a second end at the diverter, and
wherein the diverter includes a valve having an open position in which exhaled gas is diverted to bypass the $CO_2$ absorber and a shut position in which no exhaled gas is diverted to bypass the $CO_2$ absorber.

2. The $CO_2$ absorber bypass of claim 1, wherein the shunt reservoir is connected to the diverter.

3. The $CO_2$ absorber bypass of claim 2, wherein the shunt reservoir is shut when the diverter is not activated.

4. The $CO_2$ absorber bypass of claim 1, wherein the shunt reservoir is located upstream the shunt one way valve.

5. The $CO_2$ absorber bypass of claim 1, wherein the shunt reservoir is located downstream the shunt one way valve.

6. The $CO_2$ absorber bypass of claim 1, further including a cooling mechanism for cooling gas passing through the shunt.

7. The $CO_2$ absorber bypass of claim 1, wherein the diverter is automatically activated.

8. The $CO_2$ absorber bypass of claim 1, wherein at least a portion of the exhalation limb and at least a portion of the inhalation limb are co-axial.

9. An anesthesia machine for a patient, the machine comprising:
an exhalation limb for conveying exhaled gas from a patient through a reservoir;
a one way exhalation valve coupled to the exhalation limb;
an adjustable pressure limiting valve coupled to the exhalation limb;
a $CO_2$ absorber, with an entry port coupled to the adjustable pressure limiting valve and an exiting port of the $CO_2$ absorber coupled to a connector for incoming gas;
an inhalation limb coupled to the connector through a one way inhalation valve, the inhalation limb for conveying gas to the patient; and
a $CO_2$ absorber bypass comprising:
a diverter for diverting exhaled gas to bypass the $CO_2$ absorber when the diverter is activated, the diverter being located upstream the one way exhalation valve;
a shunt for conveying the diverted exhaled gas;
a coupler for connecting the shunt to the inhalation limb;
a shunt one way valve located between the coupler and the diverter;
a shunt adjustable pressure limiting valve; and
a shunt reservoir,
wherein the $CO_2$ absorber bypass allows the $CO_2$ absorber to be changed while the exhalation limb conveys exhaled gas from a patient and the inhalation limb conveys gas to the patient,
wherein the shunt is located between the coupler and the diverter with a first end at the coupler and a second end at the diverter, and
wherein the diverter includes a valve having an open position in which exhaled gas is diverted to bypass the $CO_2$ absorber and a shut position in which no exhaled gas is diverted to bypass the $CO_2$ absorber.

10. The $CO_2$ absorber bypass of claim 9, wherein the shunt reservoir is connected to the diverter.

11. The $CO_2$ absorber bypass of claim 10, wherein the shunt reservoir is shut when the diverter is not activated.

12. The $CO_2$ absorber bypass of claim 9, wherein the shunt reservoir is located upstream the shunt one way valve.

13. The $CO_2$ absorber bypass of claim 9, wherein the shunt reservoir is located downstream the shunt one way valve.

14. The $CO_2$ absorber bypass of claim 9, further including a cooling mechanism for cooling gas passing through the shunt.

15. The $CO_2$ absorber bypass of claim 9, wherein the diverter is automatically activated.

16. The $CO_2$ absorber bypass of claim 9, wherein at least a portion of the exhalation limb and at least a portion of the inhalation limb are co-axial.

17. The $CO_2$ absorber bypass of claim 1, wherein the diverter includes a flexible and disposable tubing.

18. The $CO_2$ absorber bypass of claim 1, wherein the shunt reservoir is substituted by a ventilator.

19. A $CO_2$ absorber bypass for an anesthesia machine having an exhalation limb for conveying exhaled gas from a patient through a reservoir, a one way exhalation valve, and an adjustable pressure limiting valve to an entry port of a $CO_2$ absorber, an exiting port of the $CO_2$ absorber coupled to a connector for incoming gas, the connector coupled to an inhalation limb through a one way inhalation valve, the inhalation limb for conveying gas to the patient, the $CO_2$ absorber bypass comprising:

a diverter for diverting exhaled gas to bypass the $CO_2$ absorber when the diverter is activated;
a shunt for conveying the diverted exhaled gas;
a coupler for connecting the shunt to the inhalation limb;
a shunt one way valve located between the coupler and the diverter;
a shunt adjustable pressure limiting valve; and
a shunt reservoir,
wherein the $CO_2$ absorber bypass allows the $CO_2$ absorber to be changed while the exhalation limb conveys exhaled gas from a patient and the inhalation limb conveys gas to the patient,
wherein the diverter includes flexible and disposable tubing,
wherein the shunt is located between the coupler and the diverter with a first end at the coupler and a second end at the diverter, and
wherein the diverter includes a valve having an open position in which exhaled gas is diverted to bypass the $CO_2$ absorber and a shut position in which no exhaled gas is diverted to bypass the $CO_2$ absorber.

20. The $CO_2$ absorber bypass of claim 1, wherein the shunt reservoir is located between the coupler and the diverter.

* * * * *